United States Patent
Stapleton et al.

[11] Patent Number: 5,346,700
[45] Date of Patent: Sep. 13, 1994

[54] INSECTICIDAL BAIT COMPOSITION FOR COCKROACHES

[76] Inventors: Billy J. Stapleton; Susie Stapleton, both of 401 Arrowhead Dr., Rogersville, Tenn. 37857

[21] Appl. No.: 974,364

[22] Filed: Nov. 9, 1992

Related U.S. Application Data

[63] Continuation of Ser. No. 579,381, Sep. 7, 1990, abandoned, which is a continuation-in-part of Ser. No. 395,607, Oct. 30, 1987, abandoned, which is a continuation-in-part of Ser. No. 940,093, Dec. 9, 1986, abandoned.

[51] Int. Cl.$^5$ .............................................. A01N 25/08
[52] U.S. Cl. ..................................... 424/410; 424/84; 424/409; 424/658; 424/659
[58] Field of Search ................. 424/409, 410, 84, 658, 424/659

[56] References Cited

U.S. PATENT DOCUMENTS

| | | | |
|---|---|---|---|
| 1,636,688 | 7/1927 | Harris | 424/659 X |
| 4,438,090 | 3/1984 | Brite | 424/7.1 |
| 4,617,188 | 10/1986 | Page et al. | 424/658 |
| 4,645,761 | 2/1987 | Haga et al. | 514/94 |
| 4,826,682 | 5/1989 | Sakharoua | 424/623 |
| 4,988,511 | 1/1991 | Demetre | 424/84 |
| 4,988,516 | 1/1991 | Herring | 424/659 |

FOREIGN PATENT DOCUMENTS

| | | |
|---|---|---|
| 2440339 | 3/1975 | Fed. Rep. of Germany . |
| 0834530 | 11/1938 | France . |
| 2491296 | 4/1982 | France . |
| 58-52205 | 3/1983 | Japan . |
| 58-121203 | 7/1983 | Japan . |
| 59-67209 | 4/1984 | Japan . |
| 59-128317 | 7/1984 | Japan . |
| 59-128318 | 7/1984 | Japan . |
| 59-155305 | 9/1984 | Japan . |
| 61-78705 | 4/1986 | Japan . |
| 61-137805 | 6/1986 | Japan . |

*Primary Examiner*—Thurman K. Page
*Assistant Examiner*—Robert H. Harrison
*Attorney, Agent, or Firm*—Luedeka, Neely & Graham

[57] ABSTRACT

The specification discloses an insecticidal bait composition for cockroaches and a related method of its use for the control of cockroach infestations. The composition contains boric acid in an amount between about 5 to about 40 wt. % based on the total weight of the composition together with an amount of attractant foodbaits for attracting the roaches to the composition so they will consume it. The preferred composition contains between about 30 and 35 wt. % boric acid and the foodbaits making up the remainder of the composition consist of crushed yellow onions and cane sugar each in an amount equal to about 12.5 wt. % of the remainder composition, and milk and flour each equal to about 37.5% of the remainder of the composition. The preferred composition has a gummy paste-like consistency and is particularly well-suited for application to cracks, crevices and other pest pathways.

5 Claims, No Drawings

INSECTICIDAL BAIT COMPOSITION FOR COCKROACHES

This is a continuation of application Ser. No. 07/579,381, filed Sept. 7, 1990, which is a continuation-in-part of application Ser. No. 07/395,607 filed Oct. 30, 1987, now abandoned, which is a continuation-in-part of application Ser. No. 06/940,093 filed Dec. 9, 1986, now abandoned.

BACKGROUND OF THE INVENTION

This invention relates generally to means and methods for controlling cockroaches and relates more particularly to an insecticidal bait composition and method of its application for controlling cockroaches.

Boric acid powder, i.e., sodium tetraborate, is known to be an effective agent in cockroach control. Commonly, the boric acid powder is placed in target areas in which roaches are known to frequent so that roaches are apt to walk through the powder. A roach whose body collects an amount of boric acid upon walking through the powder soon dies from the poisonous effect which the boric acid has upon the roach.

A limitation associated with insecticide compositions having a high concentration of boric acid powder relates to its typical dust-like consistency. Such compositions are normally limited to being spread upon upwardly-facing surfaces, are unsightly and are not likely to remain in place once spread across an area. Moreover, the effectiveness of such compositions may be adversely affected by humidity factors or damp environments. Also, compositions with high concentrations of boric acid are unlikely to be directly consumed by roaches. Instead, the compositions kill roaches by an indirect route as a result of the powder adhering to the roach's body.

Accordingly, it is an object of the present invention to provide a new and improved insecticide bait composition utilizing boric acid powder.

Another object of the present invention is to provide such an insecticide bait composition which is effective in operation and fast-acting.

Still another object of the present invention is to provide such an insecticide bait composition which is paste-like in form for circumventing the aforementioned limitations associated with dust-like compositions possessing a high concentration of boric acid powder.

An additional object of the invention is to provide an insecticide bait composition which avoids draw-backs associated with previous insecticide compositions containing relatively high boric acid concentrations.

SUMMARY OF THE INVENTION

This invention relates to an insecticidal bait composition for cockroaches comprising boric acid within the range of about five to about forty weight percent together with an amount of attractant foodbaits for attracting roaches to the composition so they will consume it.

When placed adjacent an area frequented by roaches, the foodbaits of the composition attract the roaches to the composition where it is ingested by the roaches. Thus, the effectiveness of the composition is not as dependant on its placement within the path of roaches or its collection on the bodies of the roaches as is the case with insecticide compositions utilizing a high concentration of boric acid powder. Moreover, the relatively lower concentration of boric acid powder of the composition of this invention is less toxic to humans than compositions possessing high concentrations of boric acid powder.

In a particular embodiment of this invention, the insecticidal bait composition possesses a paste-like consistency which, after application, dries into a relatively hard form. Because the composition is paste-like before drying to a hard form, it may be easily applied with a putty knife or similar tool within areas, such as cracks and crevices, to which dust-like compositions would ordinarily be difficult to apply. Moreover, the paste-like composition adheres to the surface to which it is applied so that the surface need not be upwardly-facing. Still further, once dried to a hardened condition, the composition is not significantly affected by humidity or damp conditions and is capable of remaining in place until totally consumed.

DETAILED DESCRIPTION OF A PREFERRED EMBODIMENT

An insecticidal bait composition for cockroaches includes an amount of boric acid powder and a remainder amount of attractant foodbaits. The boric acid in the composition may be provided as sodium tetraborate ($Na_2B_4O_7 \cdot 10 H_2O$) which is commonly known by the designation Borax (having an acute oral LD 50 in excess of 3,000 mg/kg). This component is a powder and it may be mixed with a variety of attractant foodbaits described herein to provide an effective insecticidal bait for cockroaches. The foodbaits attract the roaches to the composition where it is eaten by the roaches, and the boric acid of the composition acts as a disguised or masked poison to kill the roaches after the composition is eaten.

The foodbaits used in a preferred embodiment of the invention include an amount of raw yellow onions (medium-sized) which have been peeled and crushed in their own juice, an amount of pure cane sugar (e.g., granulated white), an amount of whole sweet milk and an amount of flour (e.g., self-rising). The aforementioned foodbaits contribute to the attraction of the roaches to the composition. Onions are advantageous for the scent and taste which they provide the composition, and the sugar and milk each serve as an attractant sweetener. Yellow onions of medium size are preferred over large ones because of the higher percentage of water normally contained within the large ones and are preferred over smaller ones from a cost standpoint.

In addition, the mixture of sugar, sweet milk, flour and onions provides the composition with a tacky, paste-like quality and a support system for holding the ingredients together. The paste-like quality of the composition enables the composition to be spread or applied to hard-to-reach areas, such as within a crack or crevice, where the composition subsequently dries and hardens within a few hours to a condition simulating that of hardened plaster. Moreover, the tackiness of the composition enables an amount of the composition to be stuck to surfaces which do not face upwardly.

Exemplary amounts of the boric acid and foodbaits comprising a preferred embodiment of the composition are as follows:

| Ingredient | Percentage by Weight |
| --- | --- |
| Boric Acid Powder | 33⅓ |

-continued

| Ingredient | Percentage by Weight |
|---|---|
| Yellow Onions (medium-sized and peeled) | 8⅓ |
| Cane Sugar | 8⅓ |
| Whole milk | 25 |
| Flour | 25 |

The composition having the ingredients listed above may be mixed in a thirty quart mixer until the composition acquires a paste-like quality whose consistency simulates that of dough batter. It has been found that the composition can be conveniently mixed in twenty-seven pound amounts by pouring into the mixer six pounds, twelve ounces of flour, nine pounds of Boric Acid powder, two pounds, four ounces of granulated sugar, two pounds, four ounces of crushed medium-sized yellow onions, and six pounds, twelve ounces of whole milk, and run the mixer at a high speed for about three minutes. The mixed composition may then be packaged into tubes or other sealed containers which prevent the mixture from hardening until applied to a surface for use or into small bait stations. For large-scale mixing it has been found that the composition is best prepared by admixing the components in a predetermined sequence and with a certain segregation. The preferred admixing procedure is to segregate the milk and crushed onions into a liquid portion and the boric acid powder, sugar and flour into a powder portion. About ½ of the liquid portion is added first and then about ½ of the powder portion is slowly admixed with the liquid portion with the stirrer on. These contents are then blended until a substantially homogenous mixture is achieved at which time the second half of the liquid portion is poured in followed by slowly admixing of the remaining powder portion. The contents are further blended until substantial homogeneity is achieved.

As mentioned earlier, the paste-like quality of the composition facilitates the application of an amount of the composition to a targeted surface. More specifically, the composition amount sticks to the surface to which it is applied so that the amount does not fall from the surface nor can it be easily removed therefrom. In addition, the composition can be applied in a manner which leaves no unsightly mess when compared to typical applications of insecticides in the form of powders and dusts. Furthermore, the aforedescribed paste-like composition is free of dust particles which may otherwise contaminate non-target areas.

Once the composition dries to a hardened condition, its effectiveness as a roach poison remains in place until entirely consumed. In addition, the hardened state of the composition, when dried, serves as a protective barrier in warm humid climates and in damp wet conditions, thus eliminating heat and/or humidity factors which may adversely effect the use of powdered insecticide compositions. This latter advantage can be readily appreciated when considering the fact that roaches ordinarily thrive in warm, moist areas.

The aforedescribed embodiment has been found to attract roaches within minutes after its application to a target area, even if it is applied in highly-lighted areas. Once a cockroach has begun feeding on the composition, it is apt to gorge itself on the composition. Nymphs, or immature cockroaches, are also known to be attracted to and ingest the composition. Of course, the roaches are unaware that the composition is a stomach poison. At least one type of roach, i.e., the German Cockroach, is known to carry its egg capsule until ready for hatching so that when the composition is eaten by this egg-carrying roach, the egg capsule is also killed.

One application of the aforedescribed composition yearly to a target area is believed to provide effective results in even the worst situations. Thus, any need to reapply in more frequent intervals, such as in monthly intervals, is obviated, and the chemical build-up in the environment which may otherwise result from more frequent applications is reduced.

Tests were performed on a variety of boric acid-to-foodbait compositions to illustrate a range of percentages, by weight, within which boric acid may be present within the composition. Results of the tests are tabulated as follows in Table 1 wherein the numerical values listed beneath the various composition makeups denote the percentage of roaches killed out of a sample amount of roaches.

TABLE 1

LOW BORIC ACID COMPOSITION
TEST RESULTS (column headings are boric acid/foodbait weight ratios)

| No. | Day 1 / 99 | 5 / 95 | 10 / 90 | 15 / 85 | 20 / 80 | 25 / 75 | 30 / 70 | 33.3 / 66.7 | 35 / 65 | 40 / 60 | 45 / 55 | 50 / 50 | 55 / 45 |
|---|---|---|---|---|---|---|---|---|---|---|---|---|---|
| 1 | 0 | 0 | 0 | 0 | 0 | 0 | 0 | 0 | 0 | 0 | 0 | 0 | 0 |
| 2 | 0 | 0 | 0 | 0 | 0 | 0 | 0 | 0 | 0 | 0 | 0 | 0 | 0 |
| 3 | 0 | 0 | 0 | 0 | 0 | 0 | 0 | 0 | 0 | 0 | 0 | 0 | 0 |
| 4 | 0 | 0 | 0 | 40 | 0 | 0 | 50 | 50 | 0 | 0 | 0 | 40 | 0 |
| 5 | 0 | 0 | 0 | 20 | 0 | 0 | 50 | 50 | 50 | 0 | 0 | 10 | 0 |
| 6 | 0 | 0 | 0 | 40 | 60 | 50 |  |  | 0 | 0 | 0 | 50 | 0 |
| 7 | 0 | 0 | 50 |  | 0 | 50 |  |  | 50 | 40 | 50 |  | 50 |

In these tests, the foodbait consisted of a mixture of milk (m) peeled and crushed raw yellow onions (medium size) (o), flour (f) and granulated white sugar (s). The percentages of these in each composition are shown below in Table 2.

TABLE 2

FOODBAIT COMPONENTS IN COMPOSITIONS OF TABLE 1

| Boric Acid % | Milk % | Onion % | Flour % | Sugar % |
|---|---|---|---|---|
| 1 | 22 | 10 | 57 | 10 |
| 5 | 26 | 16 | 34 | 19 |
| 10 | 25 | 14 | 33 | 18 |
| 15 | 24 | 12 | 32 | 17 |
| 20 | 23 | 11 | 31 | 15 |
| 25 | 22 | 10 | 30 | 13 |
| 30 | 21 | 9 | 29 | 11 |
| 33 | 22 | 8 | 29 | 8 |
| 35 | 20 | 8 | 28 | 9 |
| 40 | 19 | 7 | 27 | 7 |
| 45 | 20 | 5 | 24 | 6 |
| 50 | 29 | 4 | 13 | 4 |

TABLE 2-continued

FOODBAIT COMPONENTS IN COMPOSITIONS OF TABLE 1

| Boric Acid % | Milk % | Onion % | Flour % | Sugar % |
|---|---|---|---|---|
| 55 | 25 | 4 | 12 | 4 |

It can be seen from Table 1 above that the compositions possessing boric acid amounts of 15% 30% 33.3% and 50% provide the earliest roach kills. The composition possessing boric acid amounts of 20%, 25% and 35% provide the next earliest kills. Although not shown, the 5% boric acid composition did provide significant effectiveness after about 10 days. All compositions within the range of from about 10 to about 40% were effective to control the roaches within about a week and the roaches were observed consuming these compositions to a significant degree. It is believed that the early kills provided by the composition possessing 50% boric acid were the result of collection of boric acid on the bodies of the roaches, rather that the result of ingestion as the roaches were not observed consuming this composition to any significant degree. The test results establish a preferable range of the amount of boric acid within the composition of from about 10% to about 40%.

The compositions containing from about 30% to about 35% boric acid are particularly preferred with the 33.3% boric acid composition being most preferable. Compositions within the range of 30% to 35% provide very good kill rates and the consistency lends itself to application in the manner contemplated by the invention. Compositions with less than about 30% boric acid are thinner and compositions with more than about 35% are thicker or more powdery than is often desirable from an application standpoint. The 33.3% boric acid composition provides what is believed to be an optimal consistency with an excellent and rapid kill rate.

By utilizing an amount of boric acid in the composition of this invention which is less than that commonly utilized in powdered roach insecticides containing boric acid, the composition insecticide of the present invention is believed to be safer, i.e., less toxic to humans, than are many roach insecticides. By reducing the amount of boric acid in the composition to one-third that of pure Borax provides an acute oral LD 50 in excess of 9,000 mg/kg. Moreover, the present invention provides a composition that kills by ingestion since the roaches are not discouraged from consuming the poison as in the case of prior compositions containing greater amounts of boric acid. The presence of boric acid is effectively disguised or masked by the foodbait components so that the roaches rapidly consume lethal quantities of the composition. The consistency of the composition provides an improved method of application to areas heretofore inaccessible for long-term placement of the poison.

While several embodiments of the invention have been described in the foregoing detailed description, it will be understood that the invention is capable of numerous other forms and embodiments, rearrangements, modifications and substitutions without departing from the scope and spirit of the appended claims.

We claim:

1. An insecticidal bait composition for roach control consisting of from about 30 to about 34 weight percent boric acid, from about 8 to about 10 weight percent crushed onions, from about 6 to about 13 weight percent sugar, from about 20 to about 22 weight percent milk and from about 26 to about 30 weight percent flour, said components being thoroughly mixed together, whereby the composition has a paste consistency and adheres to surfaces to enable application of the composition into cracks and crevices, the composition drying thereafter into a relatively hard form to retain the composition in place for control of roaches in adjacent locations.

2. The composition of claim 1, wherein the concentration of boric acids is about $33\frac{1}{3}$ weight percent, the concentration of milk is about 22 weight percent, the concentration of crushed onions is about 8 weight percent, the concentration of flour is about 29 weight percent, and the concentration of sugar is about 8 weight percent.

3. The composition of claim 1, wherein the concentration of boric acid is about $33\frac{1}{3}$ weight percent, the concentration of milk is about 25 weight percent, the concentration of crushed onions is about $8\frac{1}{3}$ weight percent, the concentration of flour is about 25 weight percent, and the concentration of sugar is about $8\frac{1}{3}$ weight percent.

4. A method of controlling roach infestation which comprises providing an insecticidal bait composition consisting of from about 30 to about 34 weight percent boric acid, from about 8 to about 10 weight percent crushed onions, from about 6 to about 13 weight percent sugar, from about 20 to about 22 weight percent milk and from about 26 to about 30 weight percent flour, wherein said composition has a paste consistency, and applying said composition to cracks and crevices in walls and other structures adjacent areas of roach infestation, whereby said composition hardens in said cracks and crevices in a relatively hard mass and substantially remains therein for an extended period of time to provide an effective bait for attracting roaches adjacent said cracks and crevices to said composition wherein roaches consume said composition in said cracks and crevices in lethal amounts and the infestation of roaches in adjacent areas is thereby controlled.

5. The method of claim 4, wherein said composition is applied with a spatula, putty knife or similar tool.

* * * * *